United States Patent [19]

Hiles et al.

[11] Patent Number: 5,254,758

[45] Date of Patent: Oct. 19, 1993

[54] HYDROGENATION PROCESS

[75] Inventors: Andrew G. Hiles, Pinner; Michael W. M. Tuck, London, both of England

[73] Assignee: Davy McKee (London) Limited, London, England

[21] Appl. No.: 820,655

[22] PCT Filed: Jul. 27, 1990

[86] PCT No.: PCT/GB90/01167

§ 371 Date: Feb. 12, 1992

§ 102(e) Date: Feb. 12, 1992

[87] PCT Pub. No.: WO91/01961

PCT Pub. Date: Feb. 21, 1991

[30] Foreign Application Priority Data

Aug. 4, 1989 [GB] United Kingdom ............... 8917862

[51] Int. Cl.$^5$ ............... C07C 29/141; C07C 29/145; C07C 5/10

[52] U.S. Cl. .................... 568/881; 554/146; 564/420; 568/861; 568/863; 568/876; 568/880

[58] Field of Search .............. 568/880, 881, 884, 885, 568/814, 835, 861, 863, 876; 260/409, 413; 564/420

[56] References Cited

U.S. PATENT DOCUMENTS

| | | | |
|---|---|---|---|
| 2,549,416 | 4/1951 | Brooks et al. | 568/881 |
| 3,374,184 | 3/1968 | McEvoy et al. | 568/881 |
| 4,146,463 | 3/1979 | Radford et al. | 423/27 |
| 4,394,355 | 7/1983 | Fruge | 423/244 |
| 4,628,134 | 12/1986 | Gould et al. | 585/331 |
| 4,726,818 | 2/1988 | Yeung et al. | 55/33 |
| 4,767,604 | 8/1988 | Owen et al. | 585/331 |
| 4,899,016 | 2/1990 | Clark et al. | 585/826 |
| 4,960,960 | 10/1990 | Harrison et al. | 568/881 |
| 4,990,706 | 2/1991 | Laukonen | 570/208 |
| 4,999,089 | 3/1991 | Nakase et al. | 196/110 |
| 5,093,535 | 3/1992 | Harrison et al. | 568/881 |

FOREIGN PATENT DOCUMENTS

| | | | |
|---|---|---|---|
| 0008767 | 3/1980 | European Pat. Off. | 568/881 |
| 0073129 | 3/1983 | European Pat. Off. | 568/881 |
| 74193 | 3/1983 | European Pat. Off. | 568/881 |
| 0074193 | 3/1983 | European Pat. Off. | 568/881 |
| 0143634 | 6/1985 | European Pat. Off. | 568/881 |
| 0301853 | 2/1989 | European Pat. Off. | 568/881 |
| 8203854 | 11/1982 | World Int. Prop. O. | 568/881 |
| 8603189 | 6/1986 | World Int. Prop. O. | |
| 8607358 | 12/1986 | World Int. Prop. O. | 568/881 |
| 8805767 | 8/1988 | World Int. Prop. O. | |

Primary Examiner—Werren B. Lone
Attorney, Agent, or Firm—Rothwell, Figg, Ernst & Kurz

[57] ABSTRACT

In a hydrogenation process, an organic feedstock, such as an unsaturated organic compound containing at least one unsaturated linkage selected from $>C=C<$, $>C=O$, $-C\equiv C-$, and $-C\equiv N$, is contacted with hydrogen in a hydrogenation zone under vapor phase hydrogenation conditions in the presence of a heterogeneous hydrogenation catalyst characterized in that the hydrogenation zone includes first and second hydrogenation reactors connected in parallel, each containing a respective charge of the hydrogenation catalyst, that in a first phase of operations a vaporous mixture containing the organic feedstock and hydrogen is supplied to the first hydrogenation reactor only, that in a second phase of operation subsequent to the first phase the vaporous mixture is supplied to the second hydrogenation reactor only, and that in a third phase of operation subsequent to the second phase the vaporous mixture is supplied simultaneously both to the first hydrogenation reactor and to the second hydrogenation reactor.

9 Claims, 1 Drawing Sheet

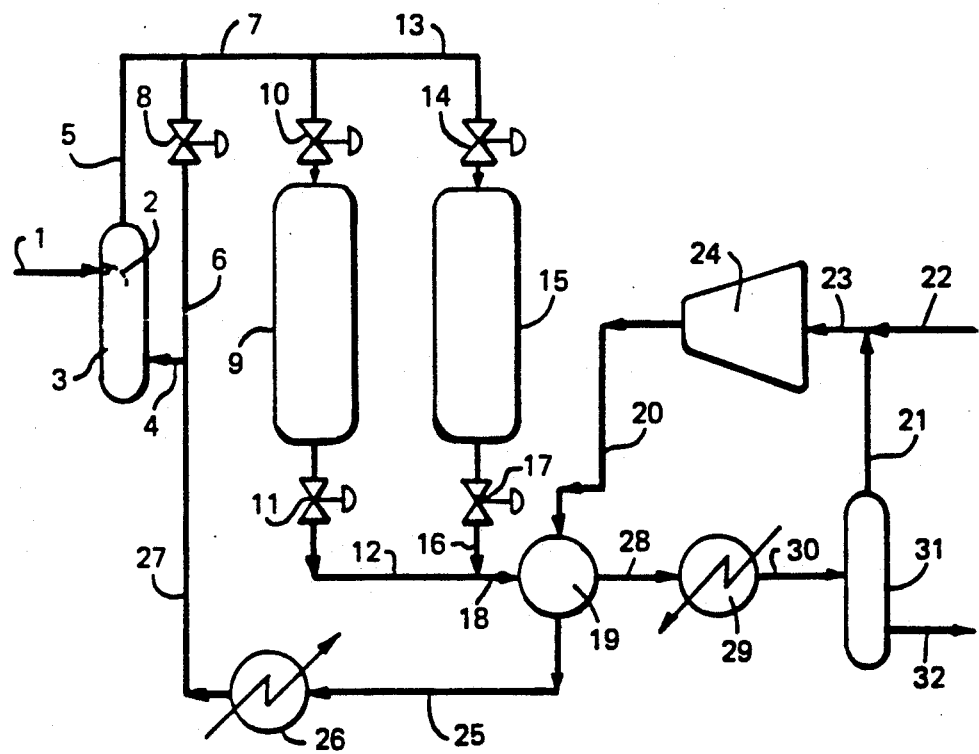

HYDROGENATION PROCESS

BACKGROUND OF THE INVENTION

1. Field of the Invention

This invention relates to a vapour phase hydrogenation process.

2. Related Art

Various hydrogenation processes have been described which utilise vapour phase conditions. In such processes a normally liquid starting material containing one or more unsaturated groups selected from

is typically vaporised in a stream of hot hydrogen or hydrogen-containing gas in a proportion such that there is formed a vaporous mixture of gas and vaporised starting material that is above the dew point of the mixture. This vaporous mixture is then passed into a hydrogenation zone containing a charge of a granular heterogeneous hydrogenation catalyst, typically a reactor containing a bed or beds of hydrogenation catalyst or a plurality of such reactors connected in series.

Another type of hydrogenation process is hydrodesulphurisation in which a hydrocarbon feedstock is contacted with hydrogen in the presence of a hydrodesulphurisation catalyst in order to reduce its sulphur content.

Examples of hydrogenation processes include hydrogenation of aldehydes to alcohols, of unsaturated hydrocarbons to saturated hydrocarbons, of ketones to secondary alcohols, of nitriles to primary amines, of alkyl esters of aliphatic monocarboxylic acids to alkanols, and of dialkyl esters of aliphatic dicarboxylic acids to aliphatic diols. Typical hydrogenation conditions include use of a pressure of from about 1 bar to about 100 bar and of a temperature of from about 40° C. to about 250° C., depending upon the nature of the hydrogenation reaction and the activity of the selected hydrogenation catalyst.

Hydrogenation is normally an exothermic reaction. Thus the hydrogenation reactor or reactors may be operated adiabatically or isothermally with external or internal cooling. Adiabatic reactors are used where possible for preference since they are usually cheaper to construct and to operate than an isothermal reactor of shell and tube design.

In a typical vapour phase hydrogenation process it is normally preferred to operate so that the temperature of the vaporous mixture in contact with the catalyst is always at least about 5° C., and even more preferably at least about 10° C., above its dew point. It is desirable to prevent contact of liquid with the catalyst because, due to the exothermic nature of the hydrogenation reaction, damage to the catalyst may result from formation of hot spots on the surface of the catalyst, leading possibly to sintering (particularly in the case of copper-containing catalysts), or from disintegration of the catalyst pellets as a result of explosive vaporisation within the pores of the catalyst pellets. Sintering is a particular hazard in the case of copper-containing hydrogenation catalysts and may result in a significant reduction in the exposed reduced copper surface area and in a consequent reduction in catalyst activity. Disintegration of catalyst pellets results in production of catalyst "fines" which causes in turn an increase in pressure drop across the catalyst bed and hence an increase in the power required to force the vaporous mixture through the hydrogenation zone. Such an increased power requirement increases the running costs for the plant operator. In addition allowance has to be made at the design stage in selecting the size of the gas recycle compressor to ensure that it can handle any increased pressure drop likely to be encountered during operation of the plant over the life of a catalyst charge. This can add significantly to the capital cost of the plant.

Vapour phase hydrogenation of aldehydes has been proposed, for example, in U.S. Pat. No. 2,549,416, and in EP-A-0008767. These proposals utilise a reduced copper oxide-zinc oxide catalyst.

Hydrogenolysis of esters to alcohols in the vapour phase is proposed in WO-A-82/03854. Again, the catalyst proposed is a reduced copper oxide-zinc oxide catalyst.

Production of butane-1, 4-diol, qamma-butyrolactone, and tetrahydrofuran by vapour phase hydrogenation of a dialkyl ester of a $C_4$ dicarboxylic acid, for example a dialkyl maleate, such as diethyl maleate, using, preferably, a reduced copper chromite catalyst, has been described in EP-A-0143634, in WO-A-86/03189, and in WO-A-86/07358.

In plants using more than one hydrogenation reactor in series, particularly those using adiabatic hydrogenation reactors connected in series, it has been recognised that it will normally be necessary to control the temperature rise across each catalyst bed in order to avoid hot spot formation and to obviate the risk of temperature runaways occurring, for example. In many cases it is disadvantageous to operate with too high an exit temperature from the catalyst bed because high exit temperatures often result in increased formation of by-products.

One way of controlling the temperature rise across a catalyst bed of an adiabatic reactor is to increase the amount of hydrogen in the circulating gas or to allow inert gases, such as nitrogen, to build up in the recirculating gas. In this way the extra gas acts as a heat sink to absorb the exothermic heat of reaction. However, the size of the gas conduits and the size of the gas recycle compressor must be increased to allow for the increased gas flow and the capital costs of the plant are increased.

Use of a plurality of adiabatic reactors in series with injection of cold shots of gas between reactors is another commonly adopted expedient. Inter-bed cooling is another method of limiting the temperature rise across an adiabatically operated catalyst bed.

Vaporisation of additional starting material in the reaction mixture exiting one reactor, prior to entry of the ensuing mixture to the next reactor of a plurality of reactors connected in series, is suggested in EP-A-0215563.

In most vapour phase hydrogenation reactions some deactivation of the catalyst is observed with passage of time in operation of a vapour phase hydrogenation plant. This loss of catalyst activity is often accompanied by an increase in pressure drop across the catalyst bed because of the production of catalyst "fines" due to disintegration of catalyst particles.

Many hydrogenation reactions require pre-reduction of the catalyst prior to commencing hydrogenation of the unsaturated organic starting material. For optimum catalyst activity care has to be taken to effect such pre-reduction of the catalyst under controlled conditions which are normally specified by the catalyst manufacturer. Such controlled pre-reduction conditions often involve use of gaseous space velocities in excess of those normally encountered during hydrogenation. Hence it is necessary to ensure at the design stage that the gas recycle compressor is large enough to provide the necessary high circulation rates required during such catalyst activation. For this reason it may be necessary to provide a gas recycle compressor that is larger, and hence is more expensive, than would be required during normal operation of the hydrogenation plant.

SUMMARY OF THE INVENTION

It would be desirable to provide a vapour phase hydrogenation process which can be carried out under adiabatic reaction conditions with minimum by-product formation using a simple hydrogenation zone and with a modest size of gas recycle compressor which can be used near its design capacity throughout all stages of the life of the catalyst charge, from pre-reduction to replacement of the catalyst charge.

The present invention accordingly seeks to provide an improved vapour phase hydrogenation process in which a single hydrogenation stage is used and in which by-product formation is minimised.

According to the present invention there is provided a vapour phase hydrogenation process in which an organic feedstock is contacted with hydrogen in a hydrogenation zone under vapour phase hydrogenation conditions in the presence of a heterogeneous hydrogenation catalyst characterised in that the hydrogenation zone includes first and second hydrogenation reactors connected in parallel, each containing a respective charge of the hydrogenation catalyst, that in a first phase of operation a vaporous mixture containing the organic feedstock and hydrogen is supplied to the first hydrogenation reactor only, that in a second phase of operation subsequent to the first phase the vaporous mixture is supplied to the second hydrogenation reactor only, and that in a third phase of operation subsequent to the second phase the vaporous mixture is supplied simultaneously both to the first hydrogenation reactor and the second hydrogenation reactor.

Examples of such a hydrogenation process include those in which the organic feedstock comprises an unsaturated organic compound containing at least one unsaturated linkage selected from

which is converted to a corresponding saturated compound in which said at least one unsaturated linkage is converted to >CH.CH<, to >CHOH, to —CH=CH— or —CH$_2$CH$_2$— and to —CH$_2$NH$_2$ respectively.

BRIEF DESCRIPTION OF THE DRAWING

FIG. 1 is a flow diagram of a plant utilizing a preferred embodiment of the process according to this invention.

DETAILED DESCRIPTION OF THE INVENTION

Typical processes in accordance with the invention include hydrogenation of aldehydes, such as n-butyraldehyde and 2-ethylhex-2-enal, to the corresponding alcohols, such as n-butanol and 2-ethylhexanol, using a reduced copper oxide-zinc oxide catalyst.

In a particularly preferred process the organic feedstock is a dialkyl ester of a C$_4$ dicarboxylic acid, for example, a dialkyl maleate, and the corresponding saturated compound is butane-1, 4-diol. In such a process the catalyst used is preferably a reduced copper chromite. The dialkyl maleate normally is a di-(C$_1$ to C$_4$ alkyl) maleate and is preferably dimethyl maleate or diethyl maleate.

Further teaching regarding the vapour phase hydrogenation of dialkyl maleates can be obtained, for example, from EP-A-0143634, WO-A-86/03189, and WO-A-86/07358.

In a typical hydrogenation process for the production of butane-1, 4-diol according to the invention the H$_2$:dialkyl maleate molar ratio in the vaporous mixture typically ranges from about 50:1 up to about 1000:1, e.g. from about 250:1 up to about 500:1. The catalyst is desirably a reduced copper chromite catalyst which has been produced by the process described in EP-A-0301853. The inlet temperature to the hydrogenation zone typically ranges from about 150° C. up to about 240° C., but is preferably in the range of from about 170° C. to about 200° C. The pressure in the hydrogenation zone may range from about 5 bar up to about 100 bar, but is preferably at least about 40 bar up to about 75 bar.

The dialkyl maleate is preferably supplied to the hydrogenation zone at a rate corresponding to a liquid hourly space velocity in the range of from about 0.1 hr$^{-1}$ up to about 0.6 hr$^{-1}$ or higher, for example up to about 1.5 hr$^{-1}$ or even up to about 3.0 hr$^{-1}$. By the term "liquid hourly space velocity" we mean the number of unit volumes of the liquid ester supplied to the vaporisation zone per unit volume of catalyst per hour. This normally corresponds to a gaseous hourly space velocity in the range of from about 2500 hr$^{-1}$ up to about 16000 hr$^{-1}$, for example up to about 85000 hr$^{-1}$, most preferably in the range of about 8000 hr$^{-1}$ to about 30000 hr$^{-1}$. By the term "gaseous hourly space velocity" we mean the number of unit volumes of vaporous mixture measured at one bar and 0° C. passed over a unit volume of catalyst per hour.

The dialkyl maleate is preferably a di-(C$_1$ to C$_4$ alkyl) maleate. The first step in its reduction is hydrogenation to the corresponding dialkyl succinate. This is an exothermic reaction.

Reduction of a dialkyl maleate to butane-1, 4-diol involves reaction of 5 moles of hydrogen with each mole of ester, according to the following equation:

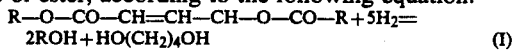

where R is an alkyl radical containing, for example, from 1 to 4 carbon atoms, such as methyl or ethyl.

In practice the reduction of a maleate ester is more complex than is suggested by equation (I) above, and results in production of variable amounts of by-products including tetrahydrofuran, gamma-butyrolactone and n-butanol. Although the reaction mechanism has not been fully elucidated yet, the currently available evidence is consistent with the following sequence:

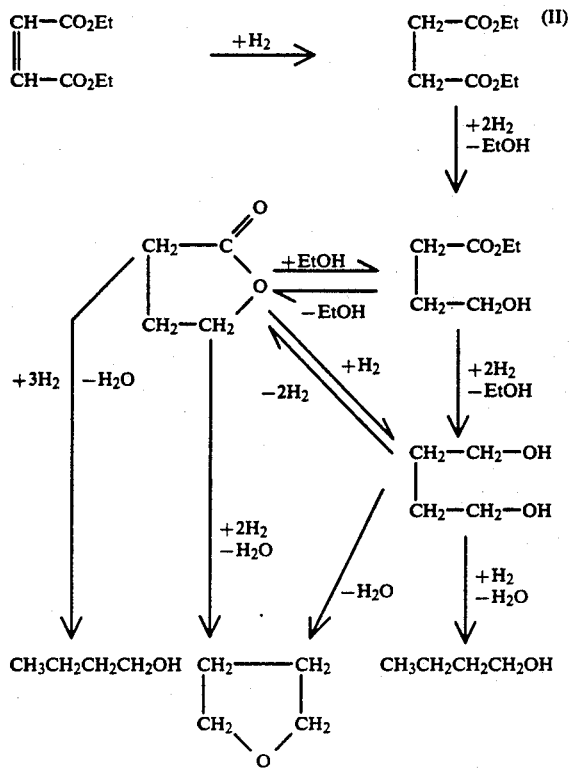

The reaction mixture exiting the hydrogenation zone typically contains, in addition to butane-1, 4-diol, also variable amounts of gamma-butyrolactone, tetrahydrofuran, and n-butanol, besides possibly traces of diethyl succinate, when the starting dialkyl maleate is diethyl maleate. As a dialkyl succinate, such as diethyl succinate, and qamma-butyrolactone are susceptible to hydrogenation to butane-1, 4-diol, these materials can be recovered in a downstream product recovery and purification section of the plant and recycled for admixture with fresh dialkyl maleate, e.g. diethyl maleate. However, tetrahydrofuran and n-butanol cannot be recycled in this way.

In passage through the hydrogenation zone the first reaction to occur is hydrogenation of dialkyl maleate to dialkyl succinate. This is an exothermic reaction. The other reactions summarised in the reaction scheme above which lead to formation of butane-1, 4-diol, gamma-butyrolactone, tetrahydrofuran and n-butanol, are much less exothermic than the hydrogenation of dialkyl maleate to dialkyl succinate.

Much of the hydrogenation activity occurs towards the front end of a catalyst bed. However a large catalyst volume is required if a high conversion per pass is required. Furthermore additional catalyst volume must be provided so as to ensure that, as the catalyst ages and/or deactivates with passage of time, the desired conversion per pass can be maintained throughout the life of the catalyst charge. Moreover a disadvantage of attempting to achieve high conversions in hydrogenation of a dialkyl maleate is that the longer that the reaction mixture remains in contact at high temperature with the catalyst, the greater the yields of tetrahydrofuran and n-butanol become.

In a hydrogenation zone containing a fresh charge of catalyst much of the hydrogenation activity occurs near the inlet end of the bed. However, in course of time, deactivation of the catalyst occurs with the result that the zone of maximum hydrogenation activity moves further away from the inlet end of the bed towards the exit end of the reactor. As the catalyst activity declines further so it becomes necessary to increase the inlet temperature to the reactor in order to maintain the desired conversion per pass. This in turn increases the exit temperature from the reactor and hence increases the exposure of the reaction mixture to the catalyst at elevated temperature. Hence increase of the inlet temperature in order to maintain the desired design throughput of the plant means that the yield of by-product tetrahydrofuran and n-butanol tends to increase with time. In addition catalyst deactivation is normally accompanied by the production of catalyst "fines" which increase the pressure drop across the catalyst bed and increase the running cost of the plant. Eventually the proportions of tetrahydrofuran and n-butanol by-products will tend to rise to economically unacceptable high values, whereupon the plant operator has to shut down the plant and discharge the catalyst before restarting the plant with a fresh catalyst charge.

In the process of the present invention two hydrogenation reactors in parallel are used, the catalyst charge being split substantially equally between the two reactors. At start-up of the plant with a fresh catalyst charge, e.g. a charge of copper chromite catalyst, the catalyst charge of the two reactors can be pre-reduced separately, following the catalyst manufacturer's instructions, thereby permitting the plant designer to design the gas recycle compressor for normal operation and it becomes unnecessary to adopt an extra large gas recycle compressor merely for use during the catalyst pre-reduction stage.

Once the catalyst charge in each hydrogenation reactor has been pre-reduced, the vaporous mixture is supplied in the first phase of operation to one only of the two hydrogenation reactors, the other hydrogenation reactor being maintained in a standby condition with its catalyst charge under an inert or a reducing gas atmosphere.

In the course of time, despite taking steps to ensure that, so far as possible, the hydrogen-containing gas and the ester are both substantially free from known catalyst poisons and catalyst deactivators, such as sulphur compounds and chlorine-containing compounds, the catalyst declines in activity with passage of time during the course of the hydrogenation process. In due course it will become necessary for the plant operator to increase the inlet temperature in order to maintain the desired output of butane-1, 4-diol. However this results also in an increase in the exit temperature from the hydrogenation reactor and an increase in the residence time at high temperature of the reaction mixture in contact with the catalyst, which in turn leads to an increase in the proportion of by-products produced, i.e. tetrahydrofuran and n-butanol. Some disintegration of the catalyst to form "fines" may also occur, such "fines" tending to block the interstices between the catalyst granules and hence tending to increase the pressure drop across the catalyst bed. As a result the plant operator may have to increase the power input to the gas recycle compressor, hence increasing the power consumption and the running costs of the process. Eventually the level of by-products will become unacceptably high. At this time the plant operator can move on to the second stage of the process.

In a second stage of the process the vaporous feed mixture is switched from the first hydrogenation reactor to the second hydrogenation reactor and this is then the sole reactor supplied with vaporous mixture during this phase of the process. As a fresh catalyst charge is being put on line, the inlet temperature to the second hydrogenation reactor can be dropped, which results in a lower exit temperature and hence a lower conversion to unwanted tetrahydrofuran and n-butanol by-products. As the catalyst charge is fresh the power supplied to the gas recycle compressor can be reduced.

In due course, during the second phase of operation of the process, deactivation of the catalyst charge in the second hydrogenation reactor takes place, as described above in relation to the first phase of operation. When the level of catalyst deactivation reaches an unacceptable degree and the by-product levels become unacceptable, then the plant operator can move on to the third phase of operation.

In the third phase of operation the vaporous feed mixture is supplied simultaneously both to the first hydrogenation reactor and also to the second hydrogenation reactor. As the available volume of catalyst is doubled, so the gaseous hourly space velocity is halved and, as the pressure drop across the catalyst beds is correspondingly reduced, the power requirement of the gas recycle compressor is reduced. As the gaseous hourly space velocity is lower, the residence time in the active hydrogenation zone, which now constitutes both reactors, not just one reactor as in the first two phases of operation, is higher and lower inlet temperatures are possible while still maintaining the desired throughput. Again, however, catalyst deactivation occurs with time and eventually the level of by-product formation becomes unacceptable, whereupon the plant operator can shut down the plant for routine maintenance and for recharging the hydrogenation reactors with fresh catalyst charges.

In designing a plant to operate using the process of the invention, it will usually be preferred to select the size of the hydrogenation reactors so that only limited conversion of diethyl maleate to butane-1, 4-diol occurs in passage therethrough. In a typical plant the conversion per pass may lie, for example, in the range of from about 50% up to about 80%.

In the designs of plant proposed in WO-A-86/03189 two reactors in series are used with inter-bed cooling. Such inter-bed cooling is necessary in order to control the temperature rise and to control the level of co-products and by-products, whilst at the same time maximising catalyst productivity and life. In contrast the present invention enables the hydrogenation reaction to be conducted in a single reaction step, which in combination with the gas recycle loop process design and with a specific catalyst management procedure permits the reaction to be controlled to give the required selectivity to products and co-products without reducing either the catalyst yield or the catalyst life.

The advantages are:

1. reduced complexity by avoiding inter stage cooling, giving easier operation and lower investment costs; and 2. reduced compressor power due to lower loop pressure drop.

In designing a plant using a single hydrogenation reactor for producing butane-1, 4-diol from a dialkyl maleate, such as dimethyl or diethyl maleate, the principal problem is associated with the control of the adiabatic temperature rise resulting from exothermic reactions, principally the hydrogenation of dialkyl maleate to dialkyl succinate. Moreover, there is an economic penalty in using low inlet temperatures since the organic materials in the vaporous feed mixture must be kept above their dew point in order to protect the catalyst against liquid condensation. This requires use of high hydrogen:organic material molar ratios. There is also an economic penalty in permitting high exit temperatures from the hydrogenation reactor since these promote increased by-product formation rates, such as n-butanol and "heavies", and particularly in the presence of excess catalyst, higher co-product formation, principally tetrahydrofuran. Hence in preference the outlet dew point is specified as low as possible, whilst still maintaining a margin above the product dew point.

These considerations determine the preferred inlet and outlet temperatures. However the problem then is that the resulting temperature range is significantly less than the adiabatic temperature rise of the overall reaction.

It is advantageous in the present invention to use an elevated pressure of, for example, from about 60 bar to about 80 bar in the production of butane-1, 4-diol from a dialkyl maleate. This is in contrast to conventional chemical engineering practice which normally seeks to operate a plant at the lowest feasible pressure. By using such elevated pressures moderation of the adiabatic temperature rise can be limited for a given size of reactor and pipework by recycling at high pressure more hydrogen than the minimum that is required to carry the feed and products to the catalyst bed as a vapour and to supply the hydrogen consumed in the reaction because, by increasing the pressure, the volume of gas to be recycled remains substantially the same.

In a further preferred process according to the invention the organic feedstock comprises an alkyl ester of an alkyl carboxylic acid, such as a methyl ester of a $C_8$ to $C_{26}$ alkylmonocarboxylic acid, the resultant product being a $C_8$ to $C_{26}$ alkanol. In such a process the catalyst may be a reduced copper oxide-zinc oxide catalyst. Typical operating pressures in this case range from about 30 bar to about 50 bar, whilst the inlet temperature to the hydrogenation zone is in the range of from about 150° C. to about 240° C., for example from about 180° C. to about 220° C.

In order that the invention may be clearly understood and readily carried into effect, a preferred process according to the invention will now be described, by way of example only, with reference to the accompanying drawing which is a simplified flow diagram of a plant designed for production of butane-1, 4-diol from diethyl maleate.

It will be appreciated by those skilled in the art that, as the drawing is diagrammatic, it will be necessary to include further items of equipment in an actual commercial plant, such as temperature sensors, pressure sensors, pressure relief valves, control valves, storage tanks, level controllers and the like. The provision of such ancillary items of equipment forms no part of the present invention and would be in accordance with conventional chemical engineering practice.

Referring to the drawing, a liquid feed stream comprising diethyl maleate is supplied in line 1 to a spray nozzle 2 of vaporiser 3 through which is passed upwardly a stream of hot hydrogen-containing gas from line 4. The resultant vaporous mixture exits vaporiser 3 in line 5 and is admixed, if desired, with further hot hydrogen-containing gas from line 6 so as to ensure that the vaporous mixture in line 7 is above its dew point, preferably at least about 5° C. above its dew point. Typically the temperature of the vaporous mixture in line 7 is about 175° C. and the $H_2$:ester molar ratio is about 275:1. Valve 8 permits control of the amount of by-pass gas passing along line 6. The rates of supply of liquid ester in line 1 and of hot hydrogen-containing gas in line 4 and the temperature of the gas in line 4 are selected so that the ester, i.e. diethyl maleate, is substantially all vaporised in vaporiser 3. Any liquid that does not vaporise will collect in the bottom of vaporiser 3 and can be drawn off through a drain line (not shown) for recycle to line 1. The level of "heavies" in this recycle stream can, if necessary, be controlled by taking a purge stream therefrom in conventional manner.

As hydrogenation of diethyl maleate produces, in addition to the desired product, butane-1, 4-diol, also qamma-butyrolactone, tetrahydrofuran and diethyl succinate as by-products, and as gamma-butyrolactone and diethyl succinate can themselves be hydrogenated to yield further butane-1, 4-diol, it is feasible to recover such qamma-butyrolactone and diethyl succinate from a downstream product recovery and purification plant (not shown) and to admix these recovered materials with fresh diethyl maleate for supply in line 1 to the vaporiser 3. In this case the conditions in vaporiser 3 and the amount of by-pass gas supplied via line 6 should be selected so that these materials, i.e. gamma-butyrolactone and diethyl succinate, do not condense out of the vaporous stream in line 7.

The hot vaporous mixture in line 7 can be fed by way of line 8 to a first hydrogenation reactor 9 which contains a charge of a granular ester hydrogenation catalyst, for example a copper chromite hydrogenation catalyst which has been suitably pre-reduced. A method of pre-reducing a copper chromite catalyst is described in EP-A-0301853. Control of flow of hot vaporous mixture through first hydrogenation reactor 9 is achieved using valve 10 in line 8 and valve 11 in exit line 12.

Alternatively the hot vaporous mixture can be fed via line 13 and valve 14 to a second hydrogenation reactor 15 which contains an essentially identical charge of catalyst to that of the first hydrogenation reactor 9. Reaction mixture exits second hydrogenation reactor via line 16 and valve 17.

If valves 10, 11, 14 and 17 are all opened, then the hot vaporous mixture can flow through both reactors 9 and 15 simultaneously.

Hot vaporous reaction mixture passes on in line 18 to heat exchanger 19 in which it gives up heat to a gas stream in line 20. This gas stream comprises recycled gas from line 21 and make-up hydrogen from line 22, the mixture in line 23 being compressed by gas recycle compressor 24.

The hot gas from heat exchanger 19 flows on in line 25 to superheater 26 to form a hot stream in line 27 which provides the gas for lines 4 and 6.

The partially cooled reaction mixture exits heat exchanger 19 in line 28 and passes through condenser 29 via line 30 to knock-out pot 31. The liquid phase is removed in line 32 and is passed on to a product recovery and purification plant (not shown). The gas phase is recycled in line 21.

The gas supplied in line 22 can be provided in any convenient manner, for example by catalytic oxidation or steam reforming of a hydrocarbon feedstock, followed by water gas shift reaction and $CO_2$ removal steps. Besides hydrogen the gas supplied in line 22 may contain one or more inert gases (e.g. $N_2$, Ar, $CH_4$ and the like). The hydrogen supply or the hydrocarbon feedstock used for generation of the hydrogen is preferably subjected to conventional purification techniques for the removal of sulphurous and halogen-containing compounds therefrom. If desired pressure swing absorption can be used to provide essentially pure hydrogen for supply in line 22.

In operation of the plant according to the process of the invention, the hydrogenation reactors 9 and 15 are charged with catalyst and, using gas supply line 22 and gas recycle compressor 24 the catalyst is pre-reduced following the manufacturer's recommended technique. Once the catalyst beds in the two reactors have been pre-reduced, valves 14 and 16 are closed and ester supply is commenced via line 1.

In the first phase of operation of the process the resulting hot vaporous mixture in line 7 is fed via line 8 through first hydrogenation reactor 9 and the reaction mixture passes on in lines 12 and 18 to heat exchanger 19.

With passage of time some deactivation of the catalyst occurs. As a result, it becomes necessary to increase the inlet temperature somewhat in order to maintain the productivity of the plant. However this means also increasing the exit temperature, which means that the yield of unwanted by-product tetrahydrofuran increases. In addition some catalyst disintegration occurs resulting in production of catalyst "fines" which increases the pressure drop across the catalyst bed or beds in the first hydrogenation reactor 9. As a result the power requirement of gas recycle compressor 24 gradually increases.

Eventually the catalyst bed or beds in first hydrogenation reactor 9 become sufficient deactivated for it to become uneconomic to continue to run the plant on the catalyst charge in first hydrogenation reactor 9.

Valves 10 and 11 are then closed and valves 14 and 17 are opened, thus permitting the hot vaporous mixture in line 7 to flow via line 13 into second hydrogenation reactor 15. The hot reaction mixture exits second hydrogenation reactor in line 16 and passes on in line 18 to heat exchanger 19. When the fresh catalyst comes on line, the inlet temperature to second hydrogenation reactor 15 can be lowered, which means that the exit temperature is also lowered, with a consequent beneficial effect upon reducing the quantity of by-product tetrahydrofuran formed. With passage of time the catalyst charge in second hydrogenation reactor 15 also becomes somewhat deactivated.

Instead of shutting down the plant to discharge the catalyst charges from both hydrogenation reactors 9 and 15, valves 10 and 11 can be opened again to permit the hot vaporous feed mixture in line 7 to flow through both reactors simultaneously. As this has the effect of halving the gaseous hourly space velocity through the catalyst beds, it is possible to reduce the inlet temperature to the beds once again with the consequent beneficial effect that the exit temperature from the catalyst beds is also reduced, thereby reducing production of by-product tetrahydrofuran. An additional factor is that the use of the two reactors 9 and 15 in parallel reduces the pressure drop across the catalyst beds. Since the gaseous hourly space velocity has been halved, this results in a reduction in the power consumption of the gas recycle compressor 24.

Eventually, following further deactivation of the catalyst in the two reactors 9 and 15, the point comes when it becomes uneconomic to continue further production of butane-1,4-diol because the rate of formation of tetrahydrofuran has reached an unacceptably high level. At this point the plant operator can shut down the plant for routine plant maintenance and for recharging the hydrogenation reactors 9 and 15 with fresh charges of catalyst.

It will be appreciated by those skilled in the art that the principles underlying the invention are not restricted to the hydrogenation of a dialkyl maleate, such as diethyl maleate, but are applicable to a wide range of hydrogenation reactions in which an organic feedstock is hydrogenated in the vapour phase. Thus, for example, the illustrated apparatus can readily be adapted for use in hydrogenation of an alkyl monocarboxylate, such as ethyl acetate or methyl laurate, according to the teachings of WO-A-82/03854. Typically such a process would be operated at about 40 bar with a feed temperature of about 190° C. and an $H_2$:ester molar ratio of about 200:1 to 400:1. Alternatively it can be adapted easily to operate a hydrogenation process in which an aldehyde is converted to an alcohol, according to the teachings of US-A-2549416 and EP-A-0008767. Typical of such processes are the hydrogenation of n-butyraldehyde to n-butonal and of 2-ethylhex-2-enal to 2-ethylhexanol. Exemplary operating conditions include use of a pressure of about 12 bar, an inlet temperature of about 135° C., and an $H_2$:aldehyde ratio of about 50:1.

I claim:

1. In a vapor phase hydrogenation process in which an organic feedstock is contacted with hydrogen in a hydrogenation zone under vapour phase hydrogenation conditions in the presence of a heterogeneous hydrogenation catalyst to produce a hydrogenation product of said organic feedstock, the improvement comprising providing a hydrogenation zone which includes first and second hydrogenation reactors connected in parallel, each containing a respective charge of the hydrogenation catalyst, supplying in a first phase of operation a vaporous feedstock mixture containing the organic feedstock and hydrogen to the first hydrogenation reactor only, recovering from the first hydrogenation reactor during said first phase of operation a vaporous product mixture comprising said hydrogenation product, supplying, in a second phase of operation subsequent to the first phase, the vaporous feedstock mixture to the second hydrogenation reactor only, recovering from the second hydrogenation reactor during said second phase of operation a vaporous product mixture comprising said hydrogenation product, supplying, in a third phase of operation subsequent to the second phase, the vaporous feedstock mixture simultaneously both to the first hydrogenation reactor and to the second hydrogenation reactor, and recovering from the first hydrogenation reactor and the second hydrogenation reactor in said third phase of operation a vaporous product mixture comprising said hydrogenation product.

2. A process according to claim 1, wherein the organic feedstock comprises a dialkyl maleate and that the catalyst is a reduced copper chromite catalyst.

3. A process according to claim 2, wherein the dialkyl maleate is dimethyl maleate or diethyl maleate.

4. A process according to claim 1, wherein the organic feedstock comprises an aldehyde and that the catalyst is a reduced copper oxide-zinc oxide catalyst.

5. A process according to claim 4, wherein the aldehyde is n-butyraldehyde and the alcohol is n-butanol.

6. A process according to claim 4, wherein the aldehyde is 2-ethylhex-2-enal and that the alcohol is 2-ethylhexanol.

7. A process according to claim 1, wherein the organic feedstock comprises an alkyl ester of an alkyl monocarboxylic acid and that the catalyst is a reduced copper oxide-zinc oxide catalyst.

8. A process according to claim 7, wherein the alkyl ester is a methyl ester of a $C_8$ to $C_{26}$ alkyl monocarboxylic acid and the alkyl alcohol is a $C_8$ to $C_{26}$ alkanol.

9. A process according to any one of claims 1 to 8, wherein the catalyst is a pre-reduced, prior to the first phase of operation, in a reducing gas atmosphere, and that the catalyst charges in the first and second hydrogenation reactors are pre-reduced simultaneously.

* * * * *

UNITED STATES PATENT AND TRADEMARK OFFICE
CERTIFICATE OF CORRECTION

PATENT NO. : 5,254,758
DATED : October 19, 1993
INVENTOR(S) : A. G. Hiles et al.

It is certified that error appears in the above-identified patent and that said Letters Patent is hereby corrected as shown below:

On title page, item [30] Foreign Application Priority Data;
"8917862" should be --8917862.8--.

Col. 9, line 19, "qamma" should be --gamma--.

Col. 9, line 23, "qamma" should be --gamma--.

Signed and Sealed this

Third Day of May, 1994

*Attest:*

BRUCE LEHMAN

*Attesting Officer*     *Commissioner of Patents and Trademarks*